(12) United States Patent
Williamson et al.

(10) Patent No.: US 6,718,209 B2
(45) Date of Patent: Apr. 6, 2004

(54) RETINAL PROSTHESIS WITH REMOTE RETURN ELECTRODE

(75) Inventors: Richard P. Williamson, Sherman Oaks, CA (US); Jerry Ok, Canyon Country, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 33 days.

(21) Appl. No.: 10/072,735

(22) Filed: Feb. 5, 2002

(65) Prior Publication Data

US 2003/0149458 A1 Aug. 7, 2003

(51) Int. Cl.[7] .................................................. A61N 1/08
(52) U.S. Cl. ...................................................... 607/54
(58) Field of Search ....................... 623/6.63; 607/53–54

(56) References Cited

U.S. PATENT DOCUMENTS

| | | | |
|---|---|---|---|
| 5,109,844 A | | 5/1992 | de Juan et al. |
| 5,935,155 A | | 8/1999 | Humayun et al. |
| 6,324,429 B1 | * | 11/2001 | Shire et al. ................... 607/54 |
| 6,427,087 B1 | * | 7/2002 | Chow et al. .................. 607/54 |
| 6,458,157 B1 | * | 10/2002 | Suaning ..................... 623/6.63 |

* cited by examiner

*Primary Examiner*—Mark Bockelman
(74) *Attorney, Agent, or Firm*—Scott B. Dunbar

(57) ABSTRACT

The present invention is an improved retinal electrode array with a remote return electrode outside of the eye. An array of stimulating electrodes is placed on the retinal surface (epiretinally) or under the retina (subretinally) and a large return electrode is placed outside of the sclera and distant from the array of stimulating electrodes. The remote return electrode promotes deeper stimulation of retinal tissue.

22 Claims, 2 Drawing Sheets

RETINAL PROSTHESIS WITH REMOTE RETURN ELECTRODE

CROSS REFERENCE TO RELATED APPLICATIONS

This application is related to U.S. patent application Ser. No. 09/761,270, Visual Prosthesis Including Enhanced Receiving and Stimulating Portion, the disclosure of which is incorporated herein by reference.

This invention was made with government support under grant No. R24EY12893-01, awarded by the National Institutes of Health. The government has certain rights in the invention.

FIELD OF THE INVENTION

The present application relates to retinal prostheses and more particularly to improved electrodes for retinal stimulation.

BACKGROUND OF THE INVENTION

It has been know since the 1700s that nerves carry their signals throughout the body by electricity. More recently, we have learned that we can partially control those signals by applying an electrical signal directly to, or in the proximity of, a nerve ending. One of the most difficult forms of nerve stimulation is the creation of artificial sight by electrically stimulating the retina.

U.S. Pat. No. 5,109,844 ("De Juan") and U.S. Pat. No. 5,935,155 ("Humuyan") disclose systems for the electrical stimulation of the retina by a retinal electrode array held against the retina. DeJuan discloses an epiretinal electrode array. Humuyan discloses a system for capturing a video image, transferring the image wirelessly into a living body and applying the image to a retinal electrode array.

The retina is structured with its light sensitive cells (rods and cones) farthest from its surface. The light sensitive cells convert light to electricity, process the electrical signal, and pass the electrical signal back toward the surface, first through bipolar cells, then through ganglion cells, and finally through nerve fibers. The nerve fibers relay the signal across the surface of the retina to the optic nerve. Simply applying an electrical signal through surface electrodes will provide the greatest stimulus to the cells closest to the surface. This will stimulate primarily nerve fibers and ganglion cells. The nerve fibers have a resistive coat which somewhat limits the signal received directly by the nerve fibers, allowing part of the signal to reach the ganglion cells. Since nerve fibers carry signal across the surface of the retina, stimulating nerve fibers can create a percept of light in a different location than intended. Stimulating between two epiretinal electrodes may cause percepts at both the anode and cathode. Much of a signal applied the retinal surface travels along the retinal surface from one electrode to the other, stimulating no cells at all.

Most retinal diseases, primarily macular degeneration and retinal pigmentosa, affect only the light receptive cells. In this case, bipolar, ganglion, and nerve fiber cells can function normally. Since a visual image is processed in the bipolar and ganglion cells, it is most advantageous to stimulate bipolar cells.

Some have addressed this problem by lifting the retina and placing an array of stimulating electrodes under the retina, and closer to the bipolar cells. The retina is a delicate organ. Implanting a subretinal electrode array is complex and dangerous surgery. Further, a subretinal electrode primarily stimulates the defective light sensitive cells and, as with epiretinal electrodes, much of the electrical signal applied to the back surface of a retina travels along that surface between electrodes. A subretinal electrode is disclosed in U.S. patent application Ser. No. 09/515,373, filed Feb. 29, 2000, entitled Method and Apparatus for Color Sight Restoration.

A new, more efficient, electrode configuration is needed to promote deep stimulation of the retina, and the bipolar cells within.

SUMMARY OF THE INVENTION

The present invention is an improved retinal electrode array with a remote return electrode outside of the eye. An array of stimulating electrodes is placed on the retinal surface (epiretinally) or under the retina (subretinally) and a large return electrode is placed outside of the sclera and distant from the array of stimulating electrodes. The remote return electrode promotes deeper stimulation of retinal tissue.

BRIEF DESCRIPTION OF THE DRAWINGS

Preferred embodiments demonstrating the various objectives and features of the invention will now be described in conjunction with the following drawings.

DETAILED DESCRIPTION OF THE PREFERRED EMBODIMENTS

Figure 1:
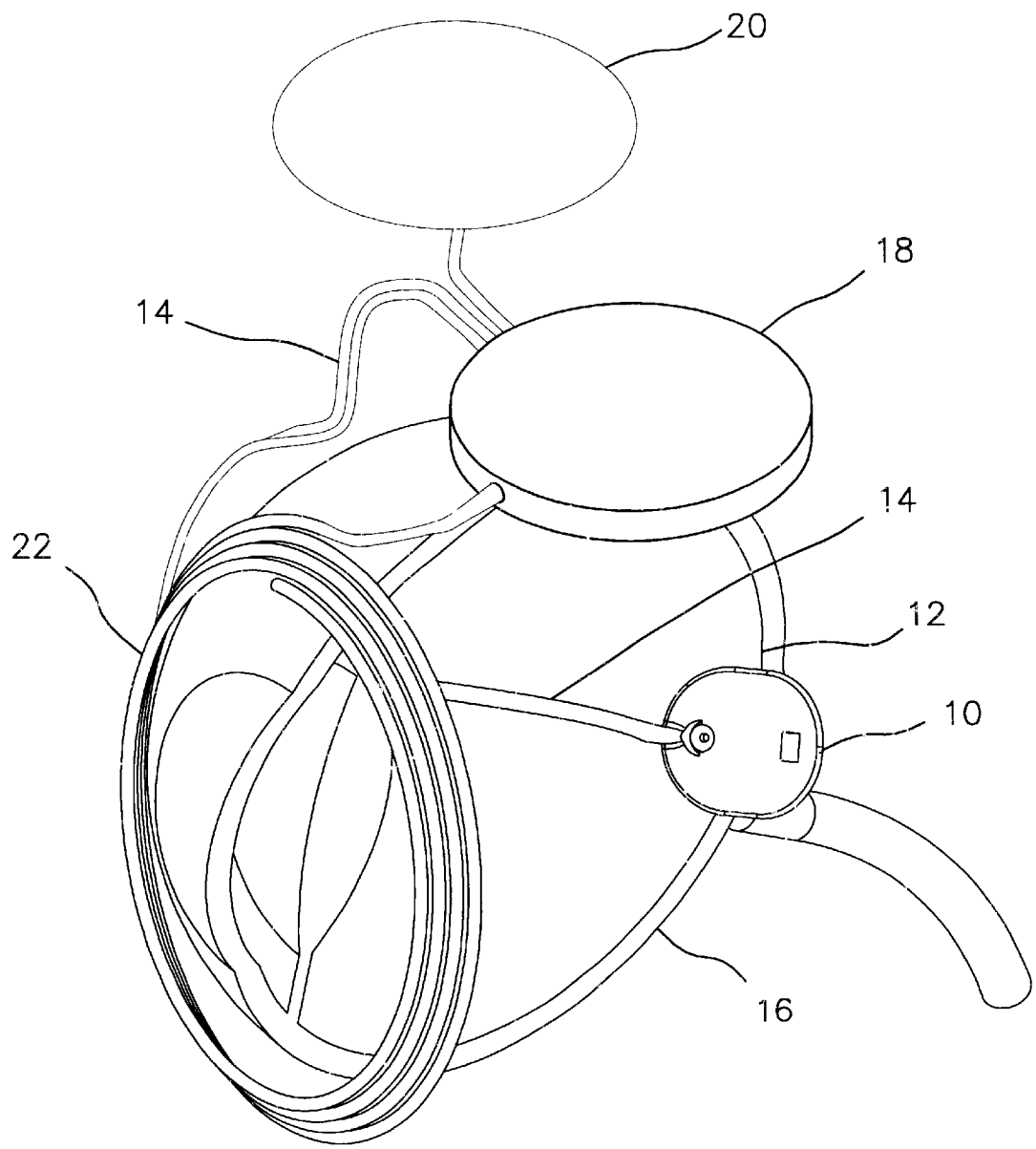
FIG. 1 shows the preferred retinal prosthesis.

FIG. 1 shows the preferred retinal prosthesis. A stimulating electrode array 10 is placed against the outer surface of a retina 12 (epiretinally). A cable 14 pierces a sclera 16 and attaches to an electronic control unit 18. The electronic control unit is attached to the sclera and moves with the sclera. A return electrode 20 is placed outside the sclera and distant from the retina 12. Electricity travels through the body between the stimulating electrode array 10 and return electrode 20, to complete an electrical circuit. The stimulating electrode array 10 is a plurality of tiny electrodes. Each electrode on the stimulating electrode array 10 is a small as possible to maximize the effect of electrical current on the retina. The return electrode 20 is quite large by comparison. The large size of the return electrode 20 minimizes the voltage developed over the electrode tissue interface. By placing the return electrode 20 remotely from the stimulating electrode array 10, current is less likely to flow along the surface of the retina, as is common in prior art designs.

Further, our current technology is not capable of making electrodes small enough or close enough together to approach the resolution of the retina. Requiring two electrodes on the retina surface (anode and cathode) for stimulation, cuts the available resolution by half. With a remote return electrode each retinal electrode can produce a separate light percept.

Since the body is primarily saline, there is little resistance to current flowing through the body. Therefore, it is not important where the return electrode is placed provided it is sufficiently large. The housing for the electronic control unit 18 can also form all or part of the return electrode 20. By providing a large remote return electrode the entire body becomes a path of current flow to the return electrode. At the retina, a signal travels from the stimulating electrode array 10 to the body. This promotes the signal to traveling through, rather than along the surface of, the retina. As the current travels through the retina, it stimulates retinal cells, including ganglion and/or bipolar cells.

The retinal prosthesis also includes a coil 22 around the front of the sclera and coupled to the electronic control unit 18. The coil 22 receives an inductive signal from an external unit (not shown). The signal includes the video information provided to the stimulating electrode array 10.

Figure 2:
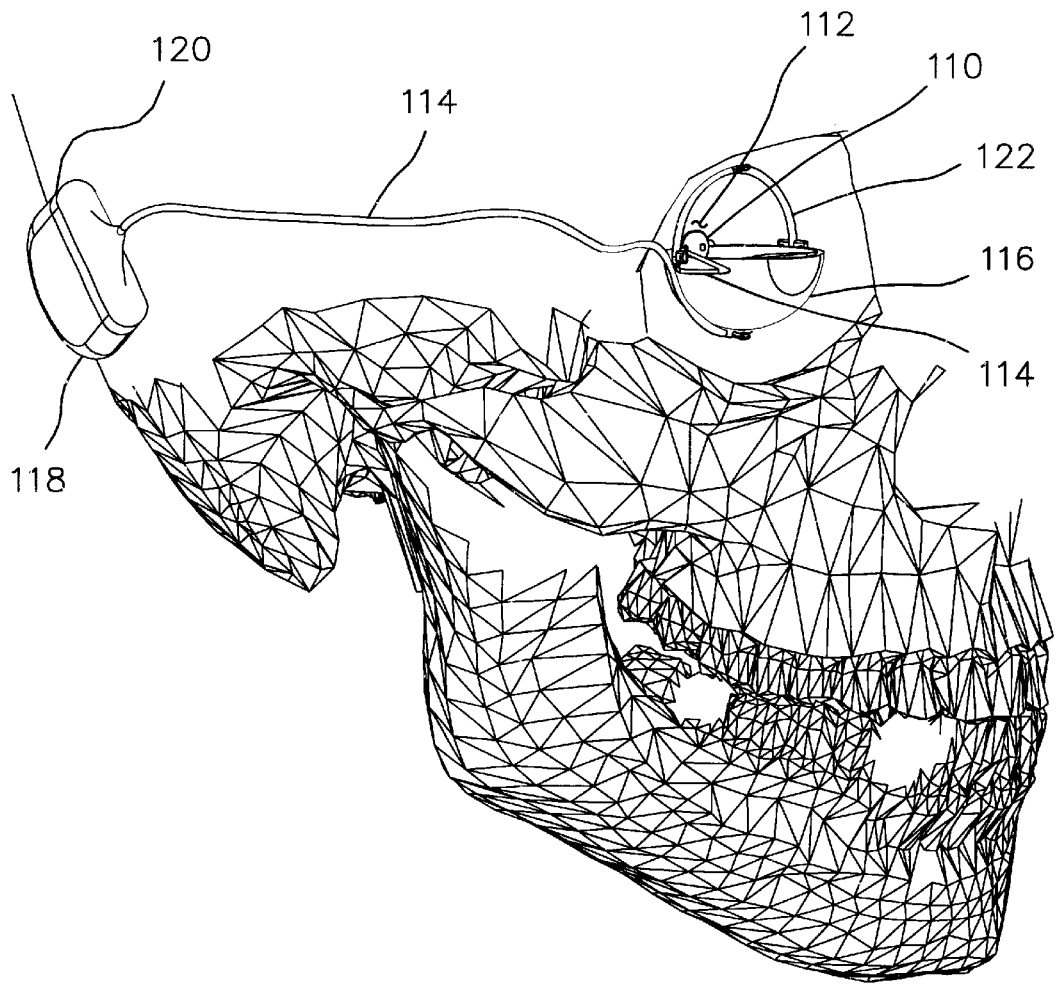
FIG. 2 shows an alternate embodiment of the preferred retinal prosthesis.

FIG. 2 shows an alternate embodiment of the preferred retinal prosthesis where an electronic control unit 118 is remote from the eye. A stimulating electrode array 110 is placed against the outer surface (epiretinal) of a retina 112. A cable 114 pierces a sclera 116 and attaches to an electronic control unit 118. Here the electronic control unit 118 is attached to the scull behind the ear. A return electrode 120 is placed on the housing for the electronic control unit 118, and distant from the retina 112. This alternate embodiment allows for a much larger electronic control unit 118. However, the cable 114 must be extremely resilient to accommodate eye movement. The difference in resistance to return electrode 120, versus return electrode 20 in FIG. 1, is negligible. In should also be noted that the present invention is not limited to a single return electrode. As an example, the return electrode 120 on the electronic control unit 118 may not be large enough to function properly as a single return electrode. It this case a separate return electrode may be added. Other issues of size and shape may make the use of multiple return electrodes necessary.

The retinal prosthesis also includes a coil 122 around the front of the sclera and coupled to the electronic control unit 118. The coil 122 receives an inductive signal from an external unit (not shown). The signal includes the video information provided to the stimulating electrode array 110.

Virtually all the resistance to current flow between stimulating epiretinal electrodes and a remote return electrode is found in the sclera. Using the device shown in FIG. 2, applicant has found the resistance of the sclera to be about 500 ohms and capacitance of the sclera to be about 300 nano-farads. This provides an excellent connection between a stimulating retinal electrode and a remote return electrode.

The present invention is also effective with a subretinal electrode. A subretinal electrode on an insulating substrate will cause current to flow through the retina even if the return electrode is physically behind the subretinal electrode. The insulating substrate prevents current flow directly to the return electrode.

Another alternate embodiment of the invention combines a retinal, or other ocular, electrode with a drug dispensing system such as a micro-fluidic device. Due to electroporation resulting from electrical stimulation, a cell is more receptive to drugs when stimulated electrically. A combined electrode drug delivery system also benefits from use of a remote return electrode by focusing the electrical current. Such a system can be used for the delivery of neurotransmitters to neural cells or for the delivery of other drugs such as steroids or anti-angiogenic factors.

The above detailed description is provided to illustrate the specific embodiments of the present invention and is not intended to be limiting. Numerous variations and modifications are possible within the scope of the present invention. The present invention is defined by the following claims.

What is claimed is:

1. A retinal prosthesis comprising:
   a stimulating electrode array adapted to be positioned inside an eye within a sclera;
   a return electrode outside of the sclera; and
   an electrical circuit coupling said stimulating electrode array with said;
   wherein said electrode array has an insulated conductor coupled thereto that is adapted to extend through the sclera to couple said array to at least said return electrode.

2. The retinal prosthesis according to claim 1, wherein said stimulating electrode array creates the perception of light.

3. The retinal prosthesis according to claim 1, wherein said return electrode provides a charge opposite to the sum of the charges on said stimulating electrode array.

4. The retinal prosthesis according to claim 1, wherein said electrical circuit is attached to the outside of the sclera.

5. The retinal prosthesis according to claim 1, wherein said electrical circuit is disposed, at least partially, outside of the sclera and said return electrode forms part of a package for said electrical circuit.

6. The retinal prosthesis according to claim 5, wherein said electrical circuit is attached to the outside of the sclera.

7. The retinal prosthesis according to claim 1, further comprising a plurality of return electrodes.

8. The retinal prosthesis according to claim 1, further comprising a drug delivery mechanism connected to said stimulating electrode array.

9. The retinal prosthesis according to claim 8, wherein current from said stimulating electrode array allows drugs from said drug delivery mechanism to pass more easily into retinal cells.

10. A retinal prosthesis comprising:
    a stimulating electrode array adapted to be positioned inside an eye within a sclera,
    an electrical circuit driving said stimulating electrode array in accordance with a visual image;
    a light receiver for receiving said visual image and providing said visual image to said electrical circuit; and
    a return electrode outside of the sclera and coupled to said; wherein said electrode array has an insulated conductor coupled thereto that is adapted to extend through the sclera to couple said electrode array to at least said return electrode.

11. The retinal prosthesis according to claim 10, wherein said return electrode provides a charge opposite to the sum of the charges on said stimulating electrode array.

12. The retinal prosthesis according to claim 10, wherein said electrical circuit is disposed, at least partially, outside of the sclera and said return electrode forms part of a package for said electrical circuit.

13. The retinal prosthesis according to claim 12, wherein said electrical circuit is attached to the outside of the sclera.

14. The retinal prosthesis according to claim 10, further comprising a plurality of return electrodes.

15. The retinal prosthesis according to claim 10, further comprising a drug delivery mechanism connected to said stimulating electrode array.

16. The retinal prosthesis according to claim 15, wherein current from said stimulating electrode array allows drugs from said drug delivery mechanism to pass more easily into retinal cells.

17. A method of passing current through a retina comprising:
    providing a stimulating electrode array near a retina;
    energizing said stimulating electrode array; and
    providing a return electrode outside of the sclera;

wherein said electrode array has an insulated conductor coupled thereto that is adapted to extend through the sclera to couple said electrode array to at least said return electrode.

18. The method according to claim 17 further comprising the step of energizing said return electrode with a charge opposite of the sum of the charges on the stimulating electrode array.

19. The method according to claim 17 further comprising the steps of:

receiving a visual image; and energizing said stimulating electrode in accordance with said visual image.

20. The method according to claim 17, further comprising the step of introducing a drug in association with said step of energizing said stimulating electrode.

21. The method according to claim 17, wherein said step of energizing said stimulating electrode array is accomplished according a received visual image.

22. The method according to claim 17, wherein said step of providing a return electrode outside of the sclera includes providing an electrical control circuit encased within said return electrode.

* * * * *

UNITED STATES PATENT AND TRADEMARK OFFICE
CERTIFICATE OF CORRECTION

PATENT NO. : 6,718,209 B2
DATED : April 6, 2004
INVENTOR(S) : Williamson et al.

It is certified that error appears in the above-identified patent and that said Letters Patent is hereby corrected as shown below:

<u>Column 4,</u>
Line 3, after "said" insert -- return electrode --
Line 6, after "said" insert -- electrode --
Line 33, after "sclera" delete "." and insert -- , --
Line 40, after "said" insert -- electrical circuit --

<u>Column 5,</u>
Lines 5 and 9, after "17" insert -- , --

Signed and Sealed this

Sixth Day of July, 2004

JON W. DUDAS
*Acting Director of the United States Patent and Trademark Office*